(12) United States Patent
Schostek et al.

(10) Patent No.: US 7,828,730 B2
(45) Date of Patent: Nov. 9, 2010

(54) DEVICE FOR HEMORRHAGE DETECTION

(75) Inventors: Sebastian Schostek, Tubingen (DE); Fabian Rieber, Stuttgart (DE); Chi-Nghia Ho, Tubingen (DE); Marc Oliver Schurr, Tubingen (DE)

(73) Assignee: Novineon Healthcare Technology Partners, GmbH (DE)

( * ) Notice: Subject to any disclaimer, the term of this patent is extended or adjusted under 35 U.S.C. 154(b) by 0 days.

(21) Appl. No.: 11/772,603

(22) Filed: Jul. 2, 2007

(65) Prior Publication Data
US 2008/0097182 A1    Apr. 24, 2008

(30) Foreign Application Priority Data

Jul. 3, 2006    (DE)    .................... 10 2006 000 318

(51) Int. Cl.
*A61B 5/00*    (2006.01)
(52) U.S. Cl. ..................................... 600/371
(58) Field of Classification Search ............... 600/371, 600/407; 356/39–41
See application file for complete search history.

(56) References Cited

U.S. PATENT DOCUMENTS

| 6,428,548 | B1 | 8/2002 | Durgin et al. | |
|---|---|---|---|---|
| 2003/0060734 | A1* | 3/2003 | Yokoi et al. | 600/593 |
| 2003/0135113 | A1* | 7/2003 | Altman et al. | 600/431 |
| 2004/0068204 | A1* | 4/2004 | Imran et al. | 600/593 |
| 2005/0148842 | A1* | 7/2005 | Wang et al. | 600/407 |
| 2006/0224165 | A1* | 10/2006 | Surti et al. | 606/142 |

FOREIGN PATENT DOCUMENTS

WO    WO 2007067952 A2 *    6/2007

* cited by examiner

*Primary Examiner*—Charles A Marmor, II
*Assistant Examiner*—Christian Jang
(74) *Attorney, Agent, or Firm*—Foley & Lardner LLP

(57) ABSTRACT

A device for hemorrhage detection comprising a detector for detecting the presence of blood, the detector being connected to a fixing, apparatus. The fixing apparatus is fixed to the inner wall of a hollow organ. The device further has a transmitting unit by which data transmitted by the detector are adapted to be transmitted to a receiving unit disposed outside the body.

14 Claims, 5 Drawing Sheets

DEVICE FOR HEMORRHAGE DETECTION

RELATED APPLICATIONS

The present application claims priority to German application No. DE 102006000318.7 filed Jul. 3, 2006, the disclosure of which is incorporated herein in its entirety.

FIELD OF THE INVENTION

The present invention relates to a device for hemorrhage detection.

BACKGROUND

Bleedings in the digestive tract may occur due to different health disturbances of the digestive tract, e.g. esophagus varices or digestive or duodenal ulcers. Even after an endoscopic treatment of such disturbances of health, there often occur recurrent bleedings that constitute a severe complication. Recurrent bleedings may occur several hours or days after a treatment, which renders their detection difficult. Bleedings in the digestive tract may lead to an acute emergency situation, since they may entail a large loss of blood if they go unnoticed. Since no continuous monitoring option is currently available, such a bleeding is often detected too late.

A known method detects bleedings by the detection of colorants that have been added to the blood in advance. Due to the limited plasma half-life time of the colorant, however this method does not work for more than a few hours, so that it is not suited for a postoperative monitoring of recurrent bleeding.

Therefore, it is an object of the present invention to provide a device for hemorrhage detection, said device being adapted to ensure a continuous monitoring of bleedings.

SUMMARY OF THE INVENTION

The object underlying the invention is achieved by a device for hemorrhage detection according to claim 1.

Further embodiments of the invention are the subject-matter of the dependent claims.

Accordingly, contemplated herein is a detecting means for detecting a presence of blood is mounted inside a hollow organ for a specific time by means of a fixing means, such as a clip. A continuous monitoring of possible bleeding sources can be realized by the detecting means being disposed directly inside the hollow organ for a specific time.

The clip may be designed such that it is transportable into the interior of a hollow organ by means of an endoscope, and is mountable to an inner wall of the hollow organ. Such a clip is known e.g. from the U.S. Pat. No. 6,428,548, another one of the applicant's applications. The fixing means need not necessarily be a clip, but may be any means that is adapted to be mounted or anchored inside a hollow organ.

The fixing means can be formed of a bio-compatible material. Additionally, the fixing means may be formed of a biodegradable material which decomposes after a certain time. In this case, due to its decomposition, the fixing means comes off from the inner wall of the organ after a certain time all by itself, and the fixing means need not be removed from the interior of the hollow organ by means of a device, such as an endoscope, but is, in the case where the hollow organ is e.g. the digestive tract, naturally excreted through the same. The biodegradable material can be selected such that, due to its decomposition, the fixing means comes off from the inner wall of the organ directly upon or shortly after the observation time desired.

The detecting means can measure a presence of blood by measuring emitted light that is absorbed or reflected by the contents in the hollow organ and the hollow organ wall, respectively. For this purpose, the detecting means emits light having a predetermined wavelength and being at least partially absorbed or reflected in the interior of the hollow organ, and detects the reflected light via a photosensitive sensor. Since blood has a characteristic absorption spectrum, which differs from the absorption spectrum of the "normal" organ contents, it can be determined due to the detected reflections whether there is any blood inside the hollow organ, or not. The detecting means comprises at least one photosensitive sensor for measuring the reflected light. This photosensitive sensor can be a photodiode or a phototransistor. Furthermore, the detecting means comprises at least one light source. In one aspect, the detecting means has at least two light sources, at least one of which emits light in the UV range, and at least one other emits light within the red range of the visible spectrum. The light source(s) can be formed as LED(s).

The device for hemorrhage detection can further comprise a transmitting unit connected to the detecting means, for sending data detected by the detecting means, and a receiving unit for receiving the data sent by the transmitting unit. The transmitting unit can be connected to the detecting means via a data-transmitting cable. As an alternative, the detecting means may be anchored or mounted to the transmitting unit, or may be integrally formed therewith.

In one embodiment, the detecting means, the transmitting unit and the fixing means are connected to each other such that they form a compact unit.

The receiving unit can be located outside the body, i.e. extracorporeally. The transmission of data from the transmitting unit to the receiving unit is effected by wireless transmission.

For representing the received signals, the receiving unit can be connected to an optical device and/or an acoustic signaling device, such as a screen or a loudspeaker. The receiving unit may also comprise a connection with a local, regional or supraregional network, e.g. via DECT, Bluetooth, WLAN, GSM, or satellite, in order to be able to transmit the signals received from the transmitting unit to third parties, e.g. a doctor or an emergency hotline/center.

The detecting means and/or the transmitting unit can be formed so as to be encapsulated. In one example, this encapsulation is composed of a body-compatible material.

The fixing means can constitute a means for stanching blood of a bleeding source. This can be realized e.g. by forming the fixing means as an endoscopic hemostasis clip.

DETAILED DESCRIPTION

The device shown in FIGS. 1-4 is a hemorrhage detecting device with parts that are examples of the elements recited in the claims. The following description, and figures, thus include examples of how a person of ordinary skill in the art can make and use the invention without imposing limitations that are not recited in the claims.

Figure 1:
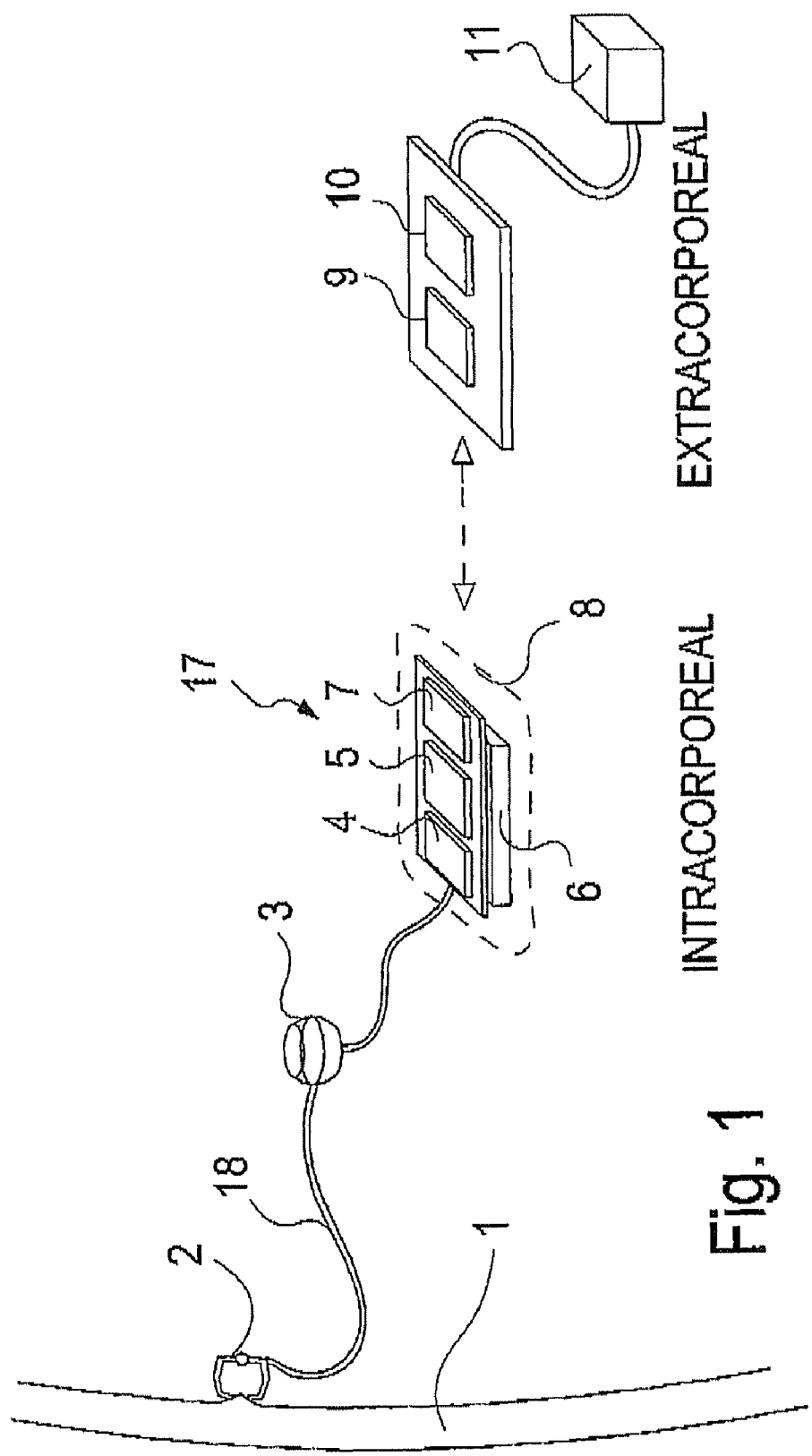
FIG. 1 shows a schematic view of the device for hemorrhage detection according to one embodiment of the invention.

As may be gathered from FIG. 1, the device for hemorrhage detection is basically composed of an intracorporeal part and an extracorporeal part. Hereinafter, the intracorporeal part shall be described first.

The intracorporeal part comprises a fixing member 2, which is a clip or anchor in this embodiment and which is mounted to an inner wall of the hollow organ, the digestive tract in this embodiment.

A detecting means 3 is connected to the clip 2 via a connecting member 18, e.g. a cord or the like. In this embodiment, the detecting means 3 is composed of two light sources, one of which emits light in the UV range, and the other emits light in the red range of the visible spectrum, and a photosensitive sensor, such as a photodiode or a phototransistor. In a pulsed manner or successively, the light sources emit light into the interior of the hollow organ in which the light is absorbed and reflected, and the photosensitive sensor detects the light transmitted or reflected in the interior.

In one embodiment, the fixing means 2 is formed as a stent-like structure. In this embodiment, the fixing means 2 is adapted to mount/fix the detecting means 3 in a tubular hollow organ, e.g. in the duodenum, for monitoring diffuse bleeding sources in the stomach or in the esophagus.

The connecting member 18 for connecting the detecting means 3 to the fixing member 2 may be formed as a cord, a wire or the like. In an embodiment, the connecting member 18 is adapted to be made of a decomposing material, e.g. a biodegradable material, which decomposes gradually. Depending on the organ and the application, the decomposition time is set such that the connecting member 18 separates the fixing member 2 from the detecting means 3 only after, preferably directly after, a reasonable observation time has elapsed. This measure permits the detecting means 3 to be excreted naturally through the digestive tract, separately from the fixing member 2.

The detecting means 3 is connected to a transmitting unit 17 by means of a data transmitting cable, so that signals are transmissible between the photosensitive sensor and the transmitting unit 17. Alternatively, the detecting means may be anchored in the transmitting unit 17 or may be unitarily formed therewith.

The transmitting unit 17 is basically composed of a data processing unit 4, an analog-digital converter 5, an energy source 6, e.g. a battery, and a transmitter 7. The data processing unit 4 controls the detecting means 3, the analog-digital converter 5 and the transmitter 7, and evaluates the data received by the photosensitive sensor. The analog-digital converter 5 converts the analog signals sent by the detecting means 3 into digital signals, and the transmitter 7 forwards the data evaluated by the data processing unit 4 to a receiving unit 9. The data transmitted by the transmitter 7 may be e.g. measured values, status information, or event signals, e.g. the event of the occurrence of a bleeding. In this embodiment, the transmitting unit 17 is surrounded by an encapsulation 8, in order to protect the elements of the transmitting unit 17. In one example, the encapsulation is formed of a body-compatible material.

The extracorporeal part is basically composed of a receiving unit 9, an interface 10, and an evaluation unit 11. The receiving unit 9 receives data sent by the transmitter 7 via a wireless transmission. The data received by the receiving unit in this way are adapted to be evaluated or represented in an evaluating unit 11 by means of the interface 10. The evaluating unit 11 may e.g. be an optical device or an acoustic signaling device, such as a display or a loudspeaker. Furthermore, the data received by the receiving unit are transmissible by means of the interface 10 to third parties, e.g. a doctor or an emergency hotline/center.

Hereinafter, the function of the device for hemorrhage detection shall now be described. The intracorporeal part composed of anchor 2, detecting means 3 and transmitting unit 17 is introduced into the digestive tract by means of an endoscope. There, the anchor 2 is fixed to an inner wall of the digestive tract by means of the endoscope. Thus, the detecting means 3 and the transmitting unit 17 are fixed in the interior of the digestive tract by the anchor 2. There, the detecting means 3 detects whether there is any blood in the digestive tract, or not. This works as follows: the two light sources of the detecting means 3, which emit light at a predetermined wavelength, are controlled by the receiving unit 4 such that each light source emits light successively, the one light source emits light in the UV range, and the other light source emits light in the red range of the visible spectrum. The light emitted by the light sources emerges into the interior of the digestive tract, and is absorbed or reflected by the contents in the interior. The photosensitive sensor in the form of a photodiode or phototransistor, formed in the detecting means 3, detects the light transmitted or reflected in the interior of the digestive tract, and produces a sensor signal on the basis of the detected light. Thus, one sensor signal is generated for each light source. If there is any blood in the interior of the digestive tract, the light emitted by the light sources is absorbed differently, as if there is no blood in the digestive tract, since blood has a specific characteristic absorption spectrum that differs from the absorption spectrum of the "normal" organ contents. Accordingly, the light reflected in the interior and received by the photosensitive sensor dependence on the presence of blood in the interior of the organ and, accordingly, also the sensor signals that are sent out by the photosensitive sensor are different depending on the presence or absence of blood. Thus, due to the different sensor signals of the photosensitive sensor, the presence or absence of blood may be detected.

In a further embodiment of the detecting means 3, the design of the detecting means 3 also allows a differentiation between the different manifestations of blood. Different manifestations of blood are e.g. clotted blood, venous blood, or arterial blood.

In a further embodiment, the detecting means comprises at least one light source for emitting light in the infrared range of the spectrum. This light source allows a differentiation between different manifestations of blood.

The sensor signals emitted by the photosensitive sensor are then transmitted to the data processing unit 4 and the analog-digital converter 5 where they are evaluated and converted, respectively. Subsequently, sensor 7 sends the evaluated and converted signals to the receiving unit 9, which is a component of the extracorporeal part and is located outside the body near the patient. The signals received by the receiving unit 9 are then outputted via an evaluating unit 11, such as a screen or a loudspeaker, that is connectable to the receiving unit 9 via an interface 10. Optionally, the evaluating unit 11 is also adapted to transmit the signals received by the receiving unit 9 via a network to third parties.

In this way, there can be continuous monitoring of whether there is blood inside the digestive tract. After a reasonable monitoring time has elapsed, e.g. two weeks, the anchor 2 drops off the organ wall all by itself. The anchor may be constructed such that, after having been applied/fixed to the organ wall, it loses its hold on the organ wall after a reasonable monitoring time, e.g. by necrosis of the gripped tissue or a rejection reaction of the gripped tissue, thus coming off the organ wall.

In a further embodiment, the anchor 2 may be made of a biodegradable material that decomposes gradually. Depending on the organ, the decomposition time is predetermined such that the anchor 2 comes off the inside wall of the organ only after lapse, preferably directly upon lapse, of a reasonable observation time. Once the anchor has come off the organ wall, the intracorporeal part is excreted naturally through the digestive tract.

Alternatively, the device is adapted to be removed again by means of an endoscope or another suitable device.

Although the embodiments are described with reference to the digestive tract, the present invention is applicable to any hollow organ. Also, a device different from an endoscope may be used for introducing the intracorporeal part and for mounting the fixing means.

A device for hemorrhage detection comprises a detecting means for detecting the presence of blood, said detecting means being connected to a fixing means. The fixing means is mounted to the inside wall of a hollow organ. The device further has a transmitting unit, by which data transmitted by the detecting means are transmissible to a receiving unit disposed outside the body.

The detecting means transmits light of specific wavelengths into the interior of the hollow organ, and measures the presence of blood preferably by measuring the intensity of the light portion absorbed by the contents of the hollow organ by means of a photosensitive sensor in the detecting means. In one example, light of different wavelengths is successively emitted and the intensity of the transmitted light portion is measured, respectively. This may be called measurement of the absorption spectrum. Different kinds of organ contents show different specific absorption spectra.

In one embodiment, the detecting means is adapted to selectively emit light in the red range of the visible spectrum as well as ultraviolet light, and to measure the absorption of red light and the absorption of ultraviolet light through the organ contents penetrated by light by means of a photosensitive sensor. For this, the photosensitive sensor may be composed of a single photo sensor sensitive to red light and ultraviolet light, or of two photo sensors, the one being sensitive to red light, and the other being sensitive to ultraviolet light. Blood has a low absorption rate for red light, but a high absorption rate for ultraviolet light. In this embodiment, this leads to the red light being absorbed to a comparatively small extent if blood is present in the organ, whereas the ultraviolet light is absorbed to a comparatively large extent. Thus, the sensor signal that depends on the intensity of the transmitted red light is the opposite of the sensor signal that depends on the intensity of the transmitted ultraviolet light (i.e. shows an opposed behavior). If, in the signal processing following the measurement, a quotient is formed from the sensor signal depending on the intensity of the transmitted red light and the sensor signal depending on the intensity of the transmitted ultraviolet light, this leads to one single parameter by means of which the presence of blood may be assumed/determined.

The quotient may be formed on the basis of measurements with light of different wavelengths as long as the absorption properties of the substance to be detected is such that it absorbs at least one wavelength strongly and at least another wavelength weakly. This need not necessarily be red light and ultraviolet light.

An embodiment of the detecting means shall be described in greater detail with reference to FIG. 2 and FIG. 3.

Figure 2:
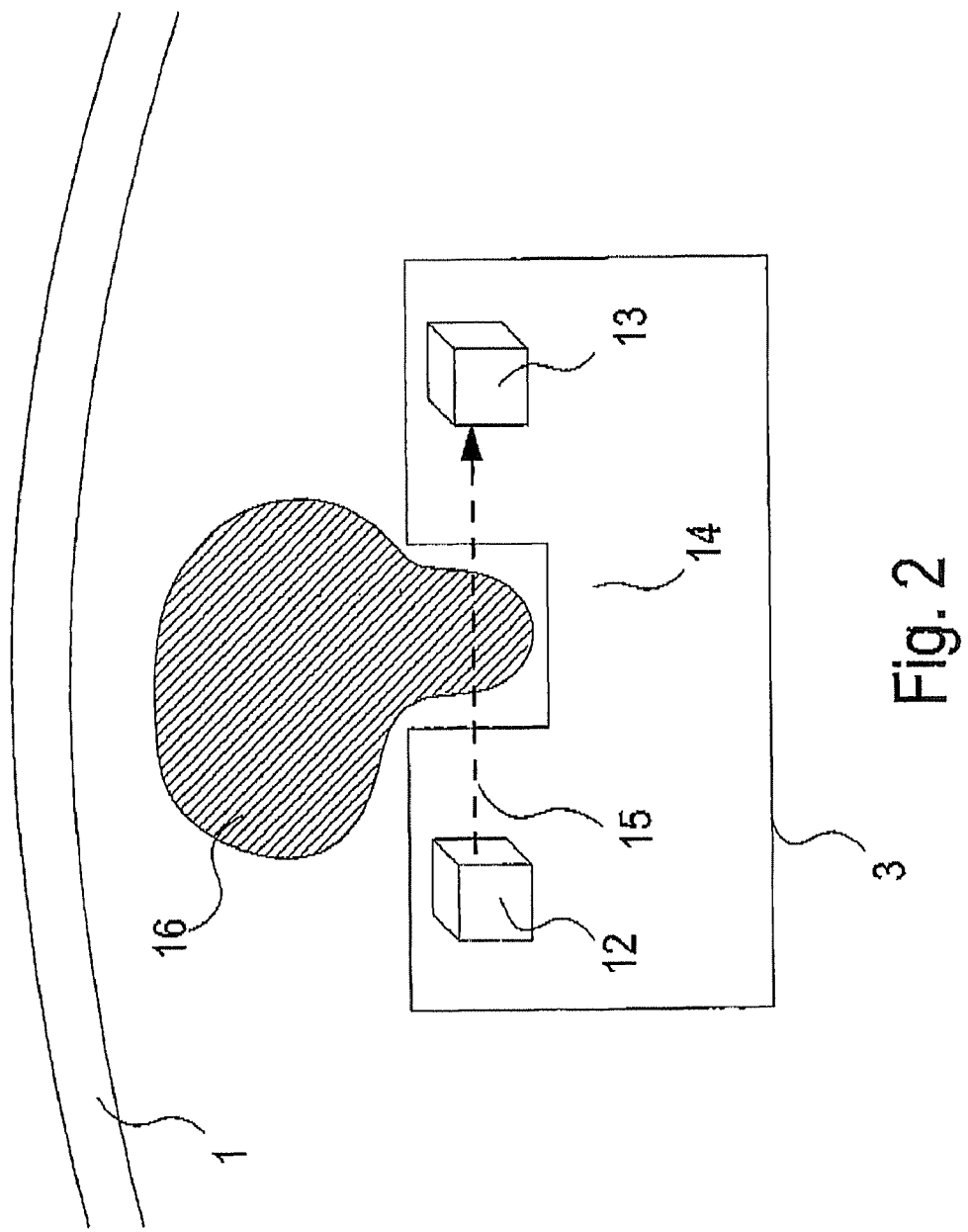
FIG. 2 is a schematic view of a detecting means of the device for hemorrhage detection according to one embodiment of the invention.

FIG. 2 shows a schematic view of the detecting means 3 of the device for hemorrhage detection according to this embodiment.

As can be gathered from FIG. 2, the detecting means 3 in this embodiment comprises a light source 12, a photosensitive sensor 13 as well as a measuring gap or recess 14. The light source 12 is capable of emitting light of at least one wavelength. For this purpose, the light source 12 is adapted to choose between emitting light of one or plural wavelengths. In one example, the light source 12 comprises one or plural LEDs for this. The light source 12, the photosensitive sensor 13 as well as the measuring gap 14 are arranged to each other such that the light 15 emitted by the light source 12 emerges from the detecting means 3 in the area of the measuring gap 14, proceeds for a specific distance outside the detecting means 3, re-enters the detecting means 3 at another point of the measuring gap 14, and subsequently falls on the photosensitive sensor 13. While the emitted light 15 proceeds outside the detecting means 3, it is able to pass through the organ contents 16, which have specific absorption properties. This allows measuring specific absorption spectra and drawing conclusions as to the nature of the organ contents 16.

The measuring gap or recess 14 may be constructed in different ways, e.g. as hollow, notch, orifice, hole, or gap.

Figure 3:
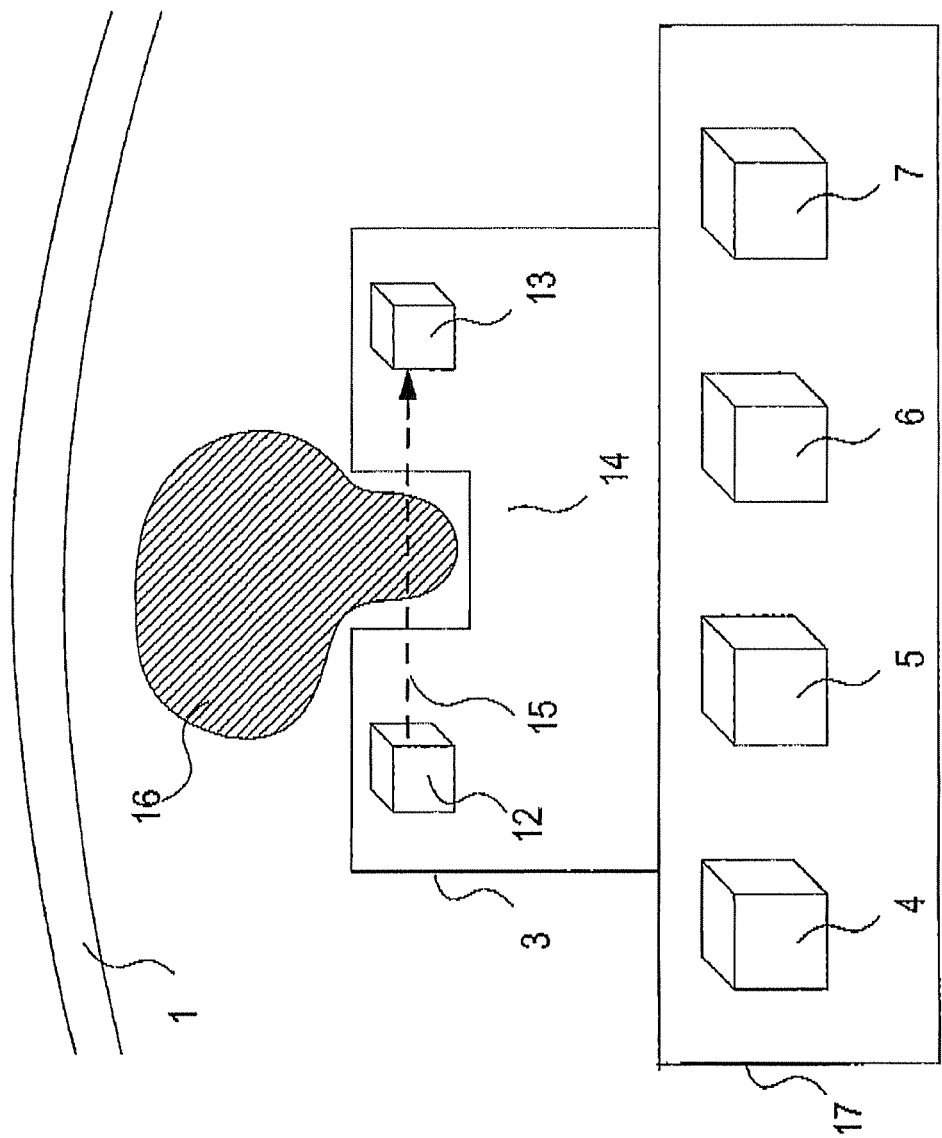
FIG. 3 is a schematic view of the detecting means and a transmitting unit of the device for hemorrhage detection according to one embodiment of the invention.

FIG. 3 shows a schematic view of the detecting means 3 as well as the transmitting unit 17 of the device for hemorrhage detection according to the embodiment.

As can be gathered from FIG. 3, the detecting means 3 in this embodiment is formed integrally with the transmitting unit 17. The transmitting unit 17 comprises a data processing unit 4, an analog-digital converter 5, an energy source 6, and a transmitter 7.

Embodiments of the device for hemorrhage detection shall be specified in greater detail in the following with reference to FIGS. 4a and 4b.

Figure 4A:
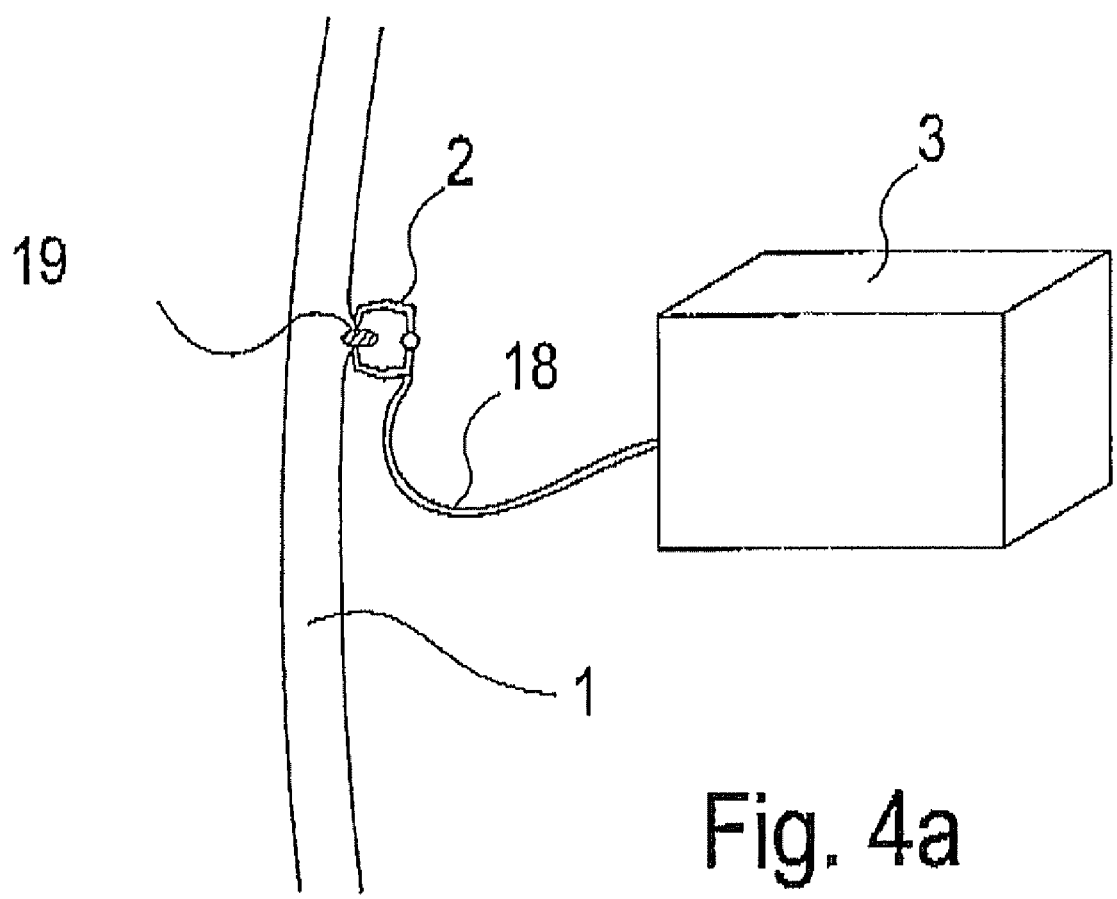
FIGS. 4a and 4b each show the device for hemorrhage detection according to one embodiment in the fixing or detection position inside a hollow organ.

FIG. 4a shows the fixing means 2, the connecting member 18, the detecting means 3, and the hollow organ wall 1. The hollow organ wall 1 shows a potential bleeding source 19. In this example of use, the fixing means 2 is mounted on the potential bleeding source 19 on the hollow organ wall 1, thus being used to treat the potential bleeding source 19 and to mount the detecting means 3. The potential bleeding source 19 may be e.g. a gastric or a duodenal ulcer.

Figure 4B:
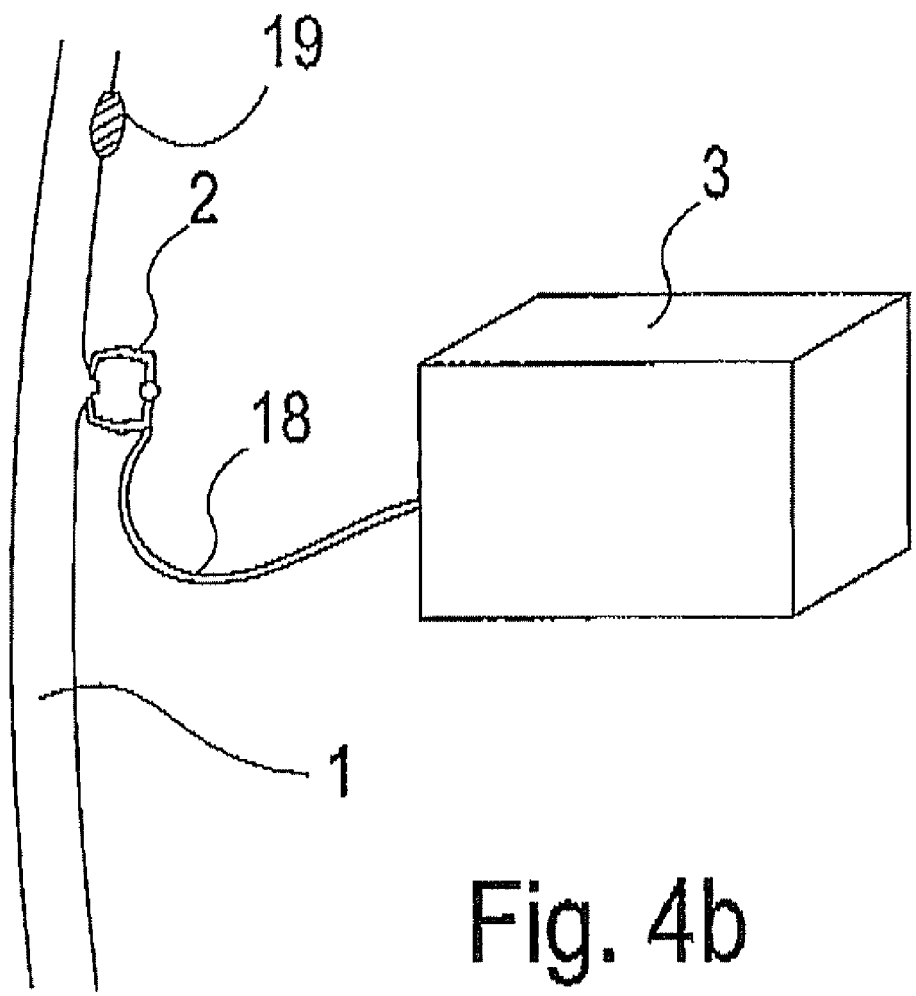

FIG. 4b shows the fixing means 2, the connecting member 18, the detecting means 3, and the hollow organ wall 1. The hollow organ wall 1 comprises a potential bleeding source 19. In this example of use, the fixing means 2 is mounted elsewhere than the bleeding source 19 on the hollow organ wall 1, thus serving for mounting the detecting means 3 in the vicinity of the potential bleeding source 19, and not for the treatment of the potential bleeding source 19. The potential bleeding source may be a structure that is highly susceptible to bleedings, e.g. a treated or untreated varix in the esophagus or stomach, or a treated or untreated gastric or duodenal ulcer. In this embodiment, the fixing means 2 may also be formed as a stent-like structure.

What is claimed is:

1. A device for hemorrhage detection, comprising a fixing means mountable inside a hollow organ, and a detecting means connected to the fixing means for detecting a presence of blood, the device further comprising:

a light source configured to emit light in an ultraviolet (UV) range and light in a red range of the visible spectrum;

at least one photosensitive sensor configured to measure a first light intensity depending on absorption in the UV range and a second light intensity depending on absorption in the red range of the visible spectrum, and to output a first sensor signal depending on the first light intensity and a second sensor signal depending on the second light intensity; and a calculation unit configured to calculate a ratio of the first sensor signal and the second sensor signal, wherein the ratio comprises a parameter determining whether blood is present or not present.

2. The device for hemorrhage detection according to claim 1, further comprising a transmitting unit for sending data detected by the detecting means, and a receiving unit for receiving the data sent by the transmitting unit.

3. The device for hemorrhage detection according to claim 2, wherein the transmitting unit is formed to be encapsulated.

4. The device for hemorrhage detection according to claim 2, wherein the transmitting unit transmits data to the receiving unit wirelessly.

5. The device for hemorrhage detection according to claim 1, wherein the fixing means is made of a biodegradable material.

6. The device for hemorrhage detection according to claim 1, wherein the connecting member is made of a biodegradable material.

7. The device for hemorrhage detection according to claim 1, wherein the photosensitive sensor is a photodiode or a phototransistor.

8. The device for hemorrhage detection according to claim 1, wherein the light source is an LED.

9. The device for hemorrhage detection according to claim 1, wherein the detecting means comprises a measuring gap.

10. The device for hemorrhage detection according to claim 9, wherein the detecting means further comprises a light source wherein light emitted by the light source is able to pass through the interior of the hollow organ in the area of the measuring gap.

11. The device for hemorrhage detection according to claim 1, wherein the fixing means comprises a means for stanching blood of a bleeding source.

12. The device for hemorrhage detection according to claim 11, wherein the means for stanching blood of a bleeding source is an endoscopic hemostasis clip.

13. The device for hemorrhage detection according to claim 1, wherein the light source is configured to emit light successively in the UV range and in the red range of the visible spectrum.

14. The device for hemorrhage detection according to claim 1, wherein the device comprises two light sources, a first light source emitting light exclusively in the UV range and a second light source emitting light exclusively in the red range of the visible spectrum.

* * * * *